US011180478B2

(12) United States Patent
Greco et al.

(10) Patent No.: US 11,180,478 B2
(45) Date of Patent: *Nov. 23, 2021

(54) PHARMACEUTICAL FORMULATIONS OF N-(2-(2-(DIMETHYLAMINO) ETHOXY)-4-METHOXY-5-((4-(1-METHYL-1H-INDOL-3-YL)PYRIMIDIN-2-YL)AMINO) PHENYL)ACRYLAMIDE AND SALTS THEREOF

(71) Applicant: Beta Pharma, Inc., Wilmington, DE (US)

(72) Inventors: Michael Nicholas Greco, Lansdale, PA (US); Michael John Costanzo, Warminster, PA (US); Michael Alan Green, Easton, PA (US); Jirong Peng, Mequon, WI (US); Victoria Lynn Wilde, Montclair, NJ (US); Don Zhang, Princeton, NJ (US)

(73) Assignee: BETA PHARMA, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,119

(22) PCT Filed: Jun. 15, 2018

(86) PCT No.: PCT/US2018/037744
§ 371 (c)(1),
(2) Date: Dec. 12, 2019

(87) PCT Pub. No.: WO2018/232235
PCT Pub. Date: Dec. 20, 2018

(65) Prior Publication Data
US 2020/0131152 A1    Apr. 30, 2020

Related U.S. Application Data (60) Provisional application No. 62/521,007, filed on Jun. 16, 2017.

(51) Int. Cl.
*A61K 31/506* (2006.01)
*C07D 403/04* (2006.01)
*A61K 47/02* (2006.01)
*A61K 47/10* (2017.01)
*A61K 47/38* (2006.01)

(52) U.S. Cl.
CPC ......... *C07D 403/04* (2013.01); *A61K 31/506* (2013.01); *A61K 47/02* (2013.01); *A61K 47/10* (2013.01); *A61K 47/38* (2013.01); *C07B 2200/13* (2013.01)

(58) Field of Classification Search
CPC .................................................. A61K 31/506
See application file for complete search history.

(56) References Cited

U.S. PATENT DOCUMENTS

| 8,946,235 B2 | 2/2015 | Butterworth et al. |
| 2008/0167463 A1 | 7/2008 | Ujagare et al. |
| 2013/0137743 A1 | 5/2013 | Liu et al. |

FOREIGN PATENT DOCUMENTS

| CA | 2966376 A1 | 5/2016 |
| WO | 2011130194 A2 | 10/2011 |
| WO | 2016094821 A2 | 6/2016 |
| WO | 2017197062 A1 | 11/2017 |
| WO | 2017218892 A1 | 12/2017 |

OTHER PUBLICATIONS

Chaudhari et al. International Journal of Advances in Pharmacy,Biology and Chemistry, vol. 1(1), Jan.-Mar. 2012.*
Caria, M.R., "Crystalline Polymorphism of Organic Compounds" Topics in Current Chemistry, Springer Berlin, DE, vol. 198, Jan. 1, 1998, pp. 163-208.
Byrn, S. et al., "Pharmaceutical Solids: A Strategic Approach to Regulatory Considerations" Pharmacautical Research, vol. 12, No. 7, Jan. 1, 1995, pp. 945-954.
International Search Report dated Sep. 24, 2018; International Application No. PCT/US2018/037744; International Filing Date Jun. 15, 2018 (3 pgs).
Written Opinion dated Sep. 24, 2018; International Application No. PCT/US2018/037744; International Filing Date Jun. 15, 2018 (5 pgs).

* cited by examiner

*Primary Examiner* — Brian E McDowell
(74) *Attorney, Agent, or Firm* — Cantor Colburn LLP (57) ABSTRACT

A pharmaceutical formulation of N-(2-(2-(dimethylamino) ethoxy)-4-methoxy-5-((4-(1-methyl-1H-indol-3-yl)pyrimidin-2-yl)amino)phenyl)acrylamide (compound 1), in particular methanesulfonic acid salt thereof, and methods of using the pharmaceutical formulation for the treatment or prevention of diseases or medical conditions mediated through mutated forms of epidermal growth factor receptor (EGFR), such as various cancers, are disclosed.

15 Claims, 8 Drawing Sheets

FIG. 1A

[scale up of mesylate-bruke-20150204.raw]                                    Peak Search Report SCAN: 4.0/39.9956/0.01972/18.6(sec), Cu(40kV,40mA), I(max)=6325, 02/05/15 14:57

PEAK: 21-pts/Parabolic Filter, Threshold=3.0, Cutoff=0.5%, BG=3/1.0, Peak-Top=Summit NOTE: Intensity = Counts, 2T(0)=0.0(°), Wavelength to Compute d-Spacing = 1.54056A(Cu/K-alpha1)

| #  | 2-Theta | d(A)    | BG  | Height | I%    | Area   | I%    | FWHM  |
|----|---------|---------|-----|--------|-------|--------|-------|-------|
| 1  | 8.536   | 10.3505 | 236 | 224    | 3.8   | 2771   | 2.7   | 0.207 |
| 2  | 9.659   | 9.1489  | 226 | 336    | 5.7   | 4853   | 4.8   | 0.242 |
| 3  | 11.140  | 7.9358  | 213 | 892    | 15.2  | 12431  | 12.2  | 0.234 |
| 4  | 12.639  | 6.9981  | 272 | 1107   | 18.8  | 13835  | 13.6  | 0.210 |
| 5  | 13.329  | 6.6370  | 261 | 479    | 8.1   | 9412   | 9.3   | 0.329 |
| 6  | 13.803  | 6.4102  | 294 | 670    | 11.4  | 6765   | 6.7   | 0.169 |
| 7  | 14.729  | 6.0093  | 276 | 1609   | 27.4  | 20216  | 19.9  | 0.211 |
| 8  | 15.538  | 5.6980  | 297 | 1941   | 33.0  | 23875  | 23.5  | 0.206 |
| 9  | 16.681  | 5.3103  | 286 | 1591   | 27.1  | 19464  | 19.2  | 0.205 |
| 10 | 17.904  | 4.9500  | 295 | 2530   | 43.0  | 33194  | 32.7  | 0.220 |
| 11 | 18.229  | 4.8650  | 307 | 458    | 7.8   | 12657  | 12.5  | 0.463 |
| 12 | 19.285  | 4.5987  | 329 | 2067   | 35.1  | 31102  | 30.6  | 0.252 |
| 13 | 19.898  | 4.4584  | 353 | 640    | 10.9  | 11071  | 10.9  | 0.290 |
| 14 | 20.943  | 4.2382  | 355 | 1295   | 22.0  | 16215  | 16.0  | 0.210 |
| 15 | 22.127  | 4.0141  | 444 | 5861   | 100.0 | 101542 | 100.0 | 0.289 |
| 16 | 23.171  | 3.8356  | 402 | 1935   | 32.9  | 37068  | 36.5  | 0.321 |
| 17 | 24.314  | 3.6577  | 353 | 875    | 14.9  | 11965  | 11.8  | 0.229 |
| 18 | 25.164  | 3.5361  | 463 | 1781   | 30.3  | 33502  | 33.0  | 0.315 |
| 19 | 25.794  | 3.4511  | 420 | 1028   | 17.5  | 30779  | 30.3  | 0.502 |
| 20 | 26.229  | 3.3949  | 561 | 557    | 9.5   | 4436   | 4.4   | 0.134 |
| 21 | 26.761  | 3.3261  | 381 | 290    | 4.9   | 3450   | 3.4   | 0.199 |
| 22 | 27.373  | 3.2555  | 357 | 969    | 16.5  | 19563  | 19.3  | 0.338 |
| 23 | 28.832  | 3.0940  | 282 | 124    | 2.1   | 3438   | 3.4   | 0.465 |
| 24 | 29.324  | 3.0432  | 295 | 280    | 4.8   | 7546   | 7.4   | 0.452 |
| 25 | 30.055  | 2.9708  | 290 | 401    | 6.8   | 6753   | 6.7   | 0.282 |
| 26 | 30.705  | 2.9093  | 307 | 77     | 1.3   | 727    | 0.7   | 0.158 |
| 27 | 31.160  | 2.8680  | 292 | 148    | 2.5   | 5510   | 5.4   | 0.624 |
| 28 | 31.535  | 2.8347  | 247 | 292    | 5.0   | 11903  | 11.7  | 0.683 |
| 29 | 32.009  | 2.7938  | 296 | 173    | 2.9   | 2323   | 2.3   | 0.225 |
| 30 | 32.635  | 2.7253  | 228 | 115    | 2.0   | 1826   | 1.8   | 0.266 |
| 31 | 33.644  | 2.6616  | 233 | 408    | 6.9   | 9725   | 9.6   | 0.400 |
| 32 | 35.777  | 2.5077  | 203 | 63     | 1.1   | 840    | 0.8   | 0.224 |
| 33 | 36.682  | 2.4479  | 215 | 183    | 3.1   | 5249   | 5.2   | 0.481 |
| 34 | 37.176  | 2.4165  | 223 | 101    | 1.7   | 3590   | 3.5   | 0.596 |
| 35 | 38.417  | 2.3412  | 244 | 456    | 7.8   | 12133  | 11.9  | 0.446 |
| 36 | 38.811  | 2.3183  | 233 | 264    | 4.5   | 8326   | 8.2   | 0.592 |

| # | 2-Theta | d(A) | BG | Height | I% | Area | I% | FWHM |
|---|---------|------|-----|--------|------|-------|-------|-------|
| 1 | 6.408 | 13.7854 | 335 | 212 | 45.5 | 3826 | 31.0 | 0.303 |
| 2 | 9.702 | 9.1083 | 274 | 333 | 71.5 | 6396 | 51.8 | 0.322 |
| 3 | 12.779 | 6.9214 | 346 | 466 | 100.0 | 9802 | 79.4 | 0.353 |
| 4 | 15.709 | 5.6397 | 387 | 268 | 57.5 | 4999 | 40.5 | 0.313 |
| 5 | 18.204 | 4.8692 | 642 | 417 | 89.5 | 9577 | 77.5 | 0.385 |
| 6 | 20.278 | 4.3762 | 696 | 216 | 46.4 | 7187 | 58.2 | 0.558 |
| 7 | 22.385 | 3.9683 | 524 | 94 | 20.2 | 4315 | 34.9 | 0.770 |
| 8 | 22.801 | 3.8969 | 524 | 89 | 19.1 | 3695 | 29.9 | 0.696 |
| 9 | 25.110 | 3.5436 | 510 | 311 | 66.7 | 11187 | 90.6 | 0.603 |
| 10 | 25.623 | 3.4738 | 499 | 289 | 62.0 | 12350 | 100.0 | 0.717 |
| 11 | 26.847 | 3.3181 | 469 | 181 | 38.8 | 4345 | 35.2 | 0.403 |
| 12 | 28.190 | 3.1630 | 392 | 72 | 15.5 | 1500 | 12.1 | 0.349 |

PHARMACEUTICAL FORMULATIONS OF N-(2-(2-(DIMETHYLAMINO)ETHOXY)-4-METHOXY-5-((4-(1-METHYL-1H-INDOL-3-YL)PYRIMIDIN-2-YL)AMINO)PHENYL)ACRYLAMIDE AND SALTS THEREOF

CROSS-REFERENCE TO RELATED APPLICATIONS

This application is the U.S. National Phase of International Patent Application No. PCT/US2018/037744, which claims priority under 35 U.S.C. § 119(e) to U.S. Provisional Application Ser. No. 62/521,007, filed on Jun. 16, 2017, the disclosures of which are incorporated herein by reference in their entirety.

FIELD OF THE INVENTION

The present invention relates to pharmaceutical formulations of N-(2-(2-(dimethylamino)ethoxy)-4-methoxy-5-((4-(1-methyl-1H-indol-3-yl)pyrimidin-2-yl)amino)phenyl)acrylamide, in particular methanesulfonic acid salt thereof, and methods of using the formulations for treating or preventing cancers.

BACKGROUND OF THE INVENTION

The epidermal growth factor receptor (EGFR, Her1, ErbB1) is a principal member of the ErbB family of four structurally-related cell surface receptors, with the other members being Her2 (Neu, ErbB2), Her3 (ErbB3), and Her4 (ErbB4). EGFR exerts its primary cellular functions through its intrinsic catalytic tyrosine protein kinase activity. The receptor is activated by binding with growth factor ligands, such as epidermal growth factor (EGF) and transforming growth factor-alpha (TGF-α), which transform the catalytically inactive EGFR monomer into catalytically active homo- and hetero-dimers. These catalytically active dimers then initiate intracellular tyrosine kinase activity, which leads to the autophosphorylation of specific EGFR tyrosine residues and elicits the downstream activation of signaling proteins. Subsequently, the signaling proteins initiate multiple signal transduction cascades (MAPK, Akt and JNK), which ultimately mediate the essential biological processes of cell growth, proliferation, motility, and survival.

EGFR is found at abnormally high levels on the surface of many types of cancer cells and increased levels of EGFR have been associated with advanced diseases, cancer spread, and poor clinical prognosis. Mutations in EGFR can lead to receptor overexpression, perpetual activation or sustained hyperactivity and result in uncontrolled cell growth, i.e., cancer. Consequently, EGFR mutations have been identified in several types of malignant tumors, including metastatic lung, head and neck, colorectal, and pancreatic cancers. In lung cancer, mutations mainly occur in exons 18 to 21, which encode the adenosine triphosphate (ATP)-binding pocket of the kinase domain. The most clinically relevant drug-sensitive EGFR mutations are deletions in exon 19 that eliminate a common amino acid motif (LREA) and point mutations in exon 21, which lead to a substitution of arginine for leucine at position 858 (L858R). Together, these two activating mutations account for nearly 85% of the EGFR mutations observed in lung cancer. Both mutations have perpetual tyrosine kinase activity and, as a result, they are oncogenic. In at least 50% of patients who are initially responsive to current therapy, disease progression is associated with the development of a secondary mutation, T790M in exon 20 of EGFR (referred to as the gatekeeper mutation). A need exists for the development of new effective and stable formulations for cancer treatment.

SUMMARY OF THE INVENTION

The present invention provides pharmaceutical formulations of N-(2-(2-(dimethylamino)ethoxy)-4-methoxy-5-((4 (4-(1-methyl-1H-indol-3-yl)pyrimidin-2-yl)amino)phenyl)acrylamide (compound 1), or a pharmaceutically acceptable salt thereof, with presence of pharmaceutically acceptable excipients, and methods of using the formulations for the treatment or prevention of diseases or medical conditions mediated through mutated forms of epidermal growth factor receptor (EGFR), such as various cancers.

In one aspect, the present invention provides a pharmaceutical formulation comprising a free base or, in a preferred embodiment, a mesylate salt (1.MeSO$_3$H, compound 2) of compound 1, as the active ingredient and one or more pharmaceutically acceptable excipients.

In some embodiments, compound 1 is in a crystalline form of mesylate salt, designated as Form 2A, having an X-ray powder diffraction pattern comprising the following 2θ values measured using CuKα radiation: 11.1°±0.2°, 12.6°±0.2°, 13.8°±0.2°, 14.7°±0.2°, 15.5°±0.2°, 16.7°±0.2°, 17.9°±0.2°, 19.3°±0.2°, 20.9°±0.2°, 22.1°±0.2°, 23.2°±0.2°, 25.2°±0.2°, and 25.8°±0.2°.

In some embodiments, compound 1 is in a crystalline form of mesylate salt (compound 2), designated as Form 2B, having an X-ray powder diffraction pattern comprising the following 2θ values measured using CuKα radiation: 9.7°±0.2°, 12.8°±0.2°, 15.7°±0.2°, 18.2°±0.2°, 20.3°±0.2°, 25.1°±0.2°, 25.6°±0.2°, and 26.8°±0.2°.

In some embodiments, the pharmaceutically acceptable excipients contain one or more fillers selected from the group consisting of monohydrate lactose, anhydrous lactose, sucrose, dextrose, mannitol, sorbitol, starch, pregelatinized starch, microcrystalline cellulose, dihydrate or anhydrous dicalcium phosphate, calcium phosphate, calcium carbonate, and calcium sulfate, wherein each of said fillers is about 15% to about 50% of the formulation by weight.

In some embodiments, the pharmaceutically acceptable excipients contain one or more disintegrants selected from the group consisting of starch, pregelatinized starch, hydroxypropyl starch, sodium starch glycolate, sodium carboxymethylcellulose, croscarmellose sodium, alginates, aluminum silicates, crospovidone, and hydroxypropyl cellulose, wherein each of said disintegrants is about 1% to about 10% of the formulation by weight.

In some embodiments, the pharmaceutically acceptable excipients contain one or more lubricants selected from the group consisting of magnesium stearate, calcium stearate, talc ("talcum powder"), polyethylene glycol ("PEG"), polymers of ethylene oxide, sodium lauryl sulfate, magnesium lauryl sulfate, sodium oleate, sodium stearyl fumarate, and silicon dioxide, wherein each of said lubricants is about 1% to about 10% of the formulation by weight.

In some embodiments, the pharmaceutically acceptable excipients contain one or more binders selected from the group consisting of acacia, cellulose derivatives (e.g.:
methylcellulose, carboxymethylcellulose, hydroxypropylmethyl cellulose, hydroxypropylcellulose, hydroxyethylcellulose), gelatin, glucose, dextrose, xylitol, polymethacrylates, polyvinylpyrrolidone, sorbitol, starch, tragacanth, xanthane resin, alginates, magnesium-aluminum silicate, polyethylene glycol (PEG), and bentonite, wherein each of said binders is about 5% to about 30% of the formulation by weight.

Another aspect of the invention provides a method of treating a disease or disorder associated with an EGFR activity, comprising administration of a therapeutically effective amount of a formulation described herein to a patient in need thereof.

In some embodiments, the disease or disorder is associated with one or more mutants of EGFR. In some embodiments, the mutant or mutants of EGFR are selected from L858R activating mutants L858R, delE746-A750, G719S; the Exon 19 deletion activating mutant; and the T790M resistance mutant. In some embodiments, the disease or disorder is a cancer.

Another aspect of the invention provides use of pharmaceutical compositions comprising methanesulfonic acid salt of compound 1 in the manufacture of medicaments for treatment of diseases or conditions, in particular various cancers, related to one or more mutants of EGFR.

Other aspects or advantages of the present invention will be better appreciated in view of the following detailed description, drawings, and claims.

BRIEF DESCRIPTION OF THE DRAWINGS

FIGS. 1A and 1B illustrate the XRPD pattern and XRPD data, respectively, of 1.MeSO$_3$H (compound 2) in crystalline Form 2A.

DETAILED DESCRIPTION OF THE INVENTION

Compound 1 effectively inhibits the kinase domain of the T790M double mutant in addition to the activating mutations and therefore overcomes the resistance observed with the currently used therapy of reversible inhibitors. Since the role of EGFR in non-small cell lung cancer (NSCLC) is well-established, compound 1 represents a novel therapeutic agent for the treatment of non-small cell lung cancer.

In some embodiments, the present invention provides a pharmaceutically acceptable salt of the compound 1 and a formulation of compound 1 or a pharmaceutically acceptable salt thereof. The formulation not only ensures a desirable pharmacokinetics profile but also demonstrates excellent stability over an extended period.

As used herein, the term "pharmaceutically acceptable excipient or carrier" refers to any substance, not itself a therapeutic agent, used as a carrier, diluent, adjuvant, binder, lubricant, disintegrant and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in *Remington: The Science and Practice of Pharmacy*, 21$^{st}$ Ed. (Lippincott Williams & Wilkins, Baltimore, Md., 2005) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners, or the like.

As used herein, the term "subject" or "patient" refers to a mammal, including but not limited to, a human. Hence, the methods disclosed herein can be useful in human therapy and veterinary applications. In one embodiment, the patient is a mammal. In some embodiments, the patient is a human. In some embodiments, the patient is a mammalian animal such as dogs, cats, and horses.

As used herein, the articles "a" and "an" as used herein refers to "one or more" or "at least one," unless otherwise indicated. That is, reference to any element or component of the present invention by the indefinite article "a" or "an" does not exclude the possibility that more than one element or component is present.

The term "about" is used herein to indicate that certain preferred operating ranges, such as ranges for molar ratios for material amounts, and temperature, are not fixedly determined. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The term "treating" or "treatment" refers to: (i) inhibiting the disease, disorder, or condition, i.e., arresting its development; or (ii) relieving the disease, disorder, or condition, i.e., causing regression of the disease, disorder, and/or condition. Thus, in one embodiment, "treating" or "treatment" refers to ameliorating a disease or disorder, which may include ameliorating one or more physical parameters, though may be indiscernible by the subject being treated. In another embodiment, "treating" or "treatment" includes modulating the disease or disorder, either physically (e.g., stabilization of a discernible symptom) or physiologically (e.g., stabilization of a physical parameter) or both.

Pharmaceutical Formulations

An aspect of the invention provides pharmaceutical formulations comprising compound 1 or a pharmaceutically acceptable salt thereof, and one or more pharmaceutically acceptable excipients. In some embodiments, the active ingredient compound 1 is in a free base form in the formulation. In some embodiments, the active ingredient is a pharmaceutically acceptable salt of compound 1. Non-limiting examples of the acid suitable for forming the salt include methanesulfonic acid, hydrochloride acid, sulfuric acid, toluenesulfonic acid, and citric acid. These salts, among others, and respective crystalline forms have been described in International Application No. PCT/US2017/037872 by the Applicant, which is incorporated herein by reference in its entirety.

The amount of compound 1 or a pharmaceutically acceptable salt thereof in the formulation depends on factors such as the target treatment, the administration regimen, and the actual excipients. However, exemplary ranges for compound 1 or a pharmaceutically acceptable salt thereof in the formulation include about 10% to about 50%, about 10% to about 30%, about 15% to about 35%, about 15% to about 30%, and about 15% and about 25% by weight.

In some preferred embodiments, the active ingredient in the formulation is a mesylate salt of compound 1 (i.e., the compound 2).

2

Figure 1A:
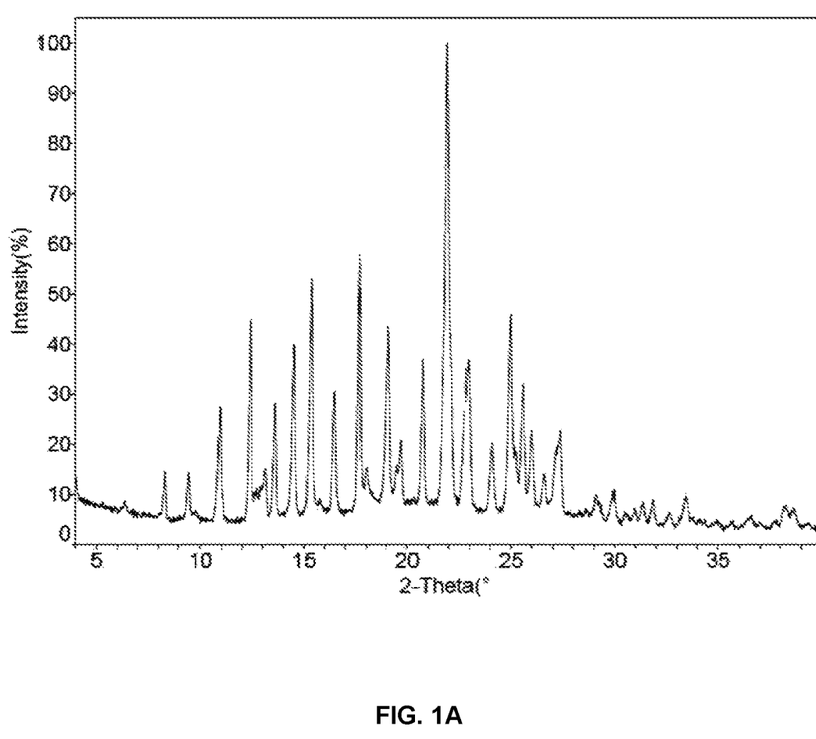
Figure 2:
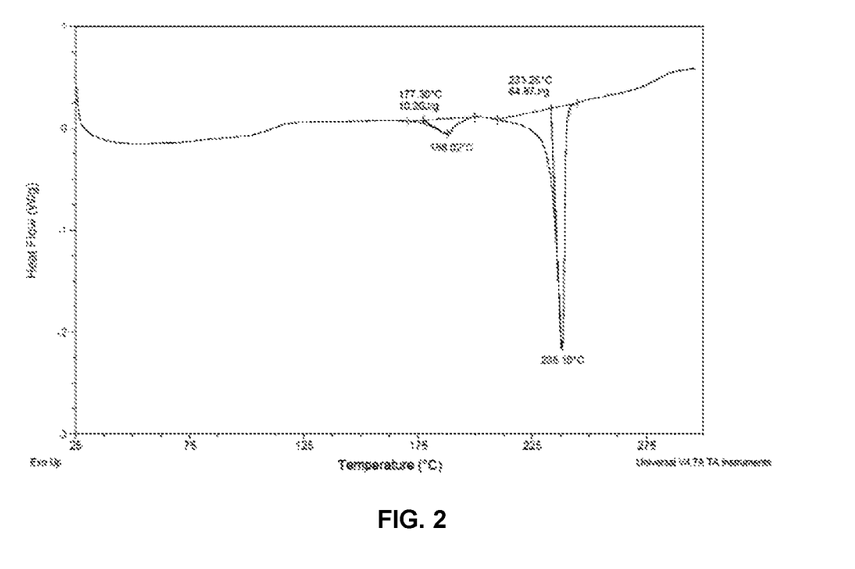
FIG. 2 illustrates DSC thermogram of compound 2 (Form 2A).
Figure 3:
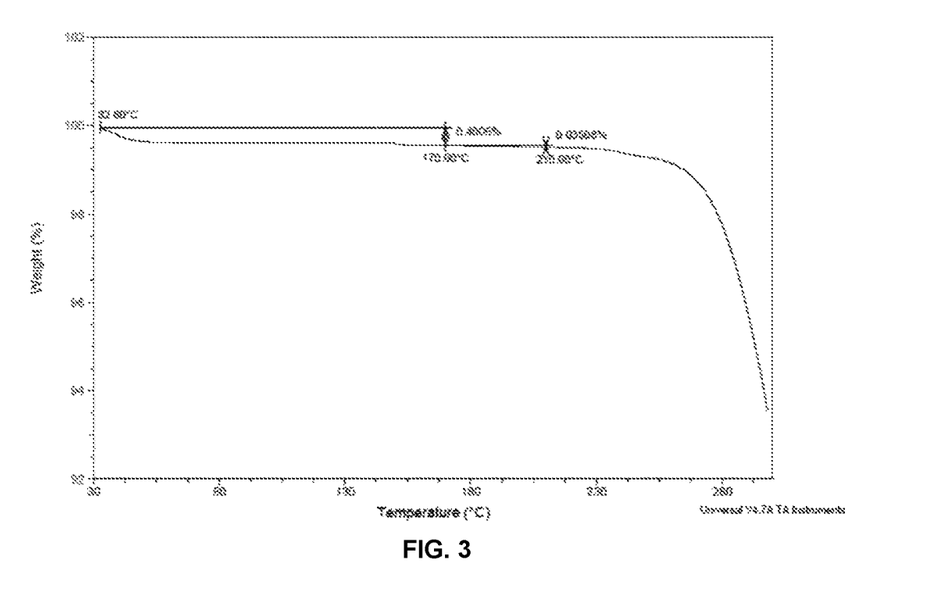
FIG. 3 illustrates TGA thermogram of compound 2 (Form 2A).

In one embodiment, the present invention provides a pharmaceutical formulation comprising a crystalline form of mesylate salt designated as Form 2A, having an X-ray powder diffraction pattern comprising the following 2θ values measured using CuKα radiation: 12.6°±0.2°, 15.5°±0.2°, 17.9°±0.2°, 22.1°±0.2°, and 25.2°±0.2°. The crystalline Form 2A has one or more of the following characteristics:

(a) the X-ray powder diffraction pattern containing two or more of the following 2θ values measured using CuKα radiation: 11.1°±0.2°, 13.8°±0.2°, 14.7°±0.2°, 16.7°±0.2°, 19.3°±0.2°, 20.9°±0.2°, 23.2°±0.2°, and 25.8°±0.2°;

(b) a melting point with an onset temperature at about 233.3° C. and/or a peak temperature at about 238.1° C. as measured by differential scanning calorimetry;

(c) an X-ray powder diffraction pattern substantially as depicted in FIG. 1;

(d) a differential scanning calorimetric thermogram substantially as depicted in FIG. 2; and/or (e) a thermal gravimetric analysis thermogram substantially as depicted in FIG. 3.

Figure 4A:
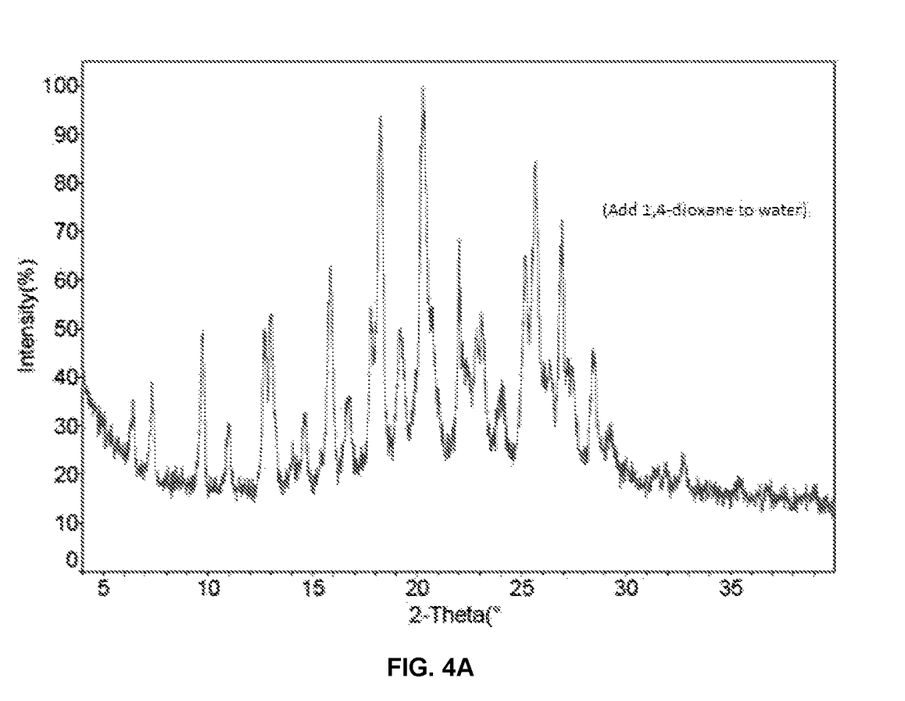
FIGS. 4A and 4B illustrate the XRPD pattern and XRPD data, respectively, of compound 2 in crystalline Form 2B.
Figure 4B:
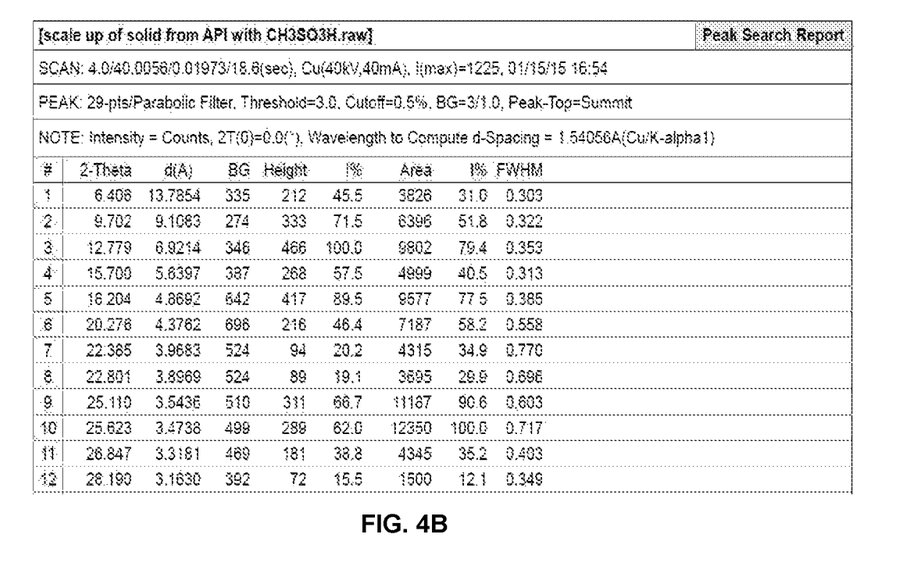
Figure 5:
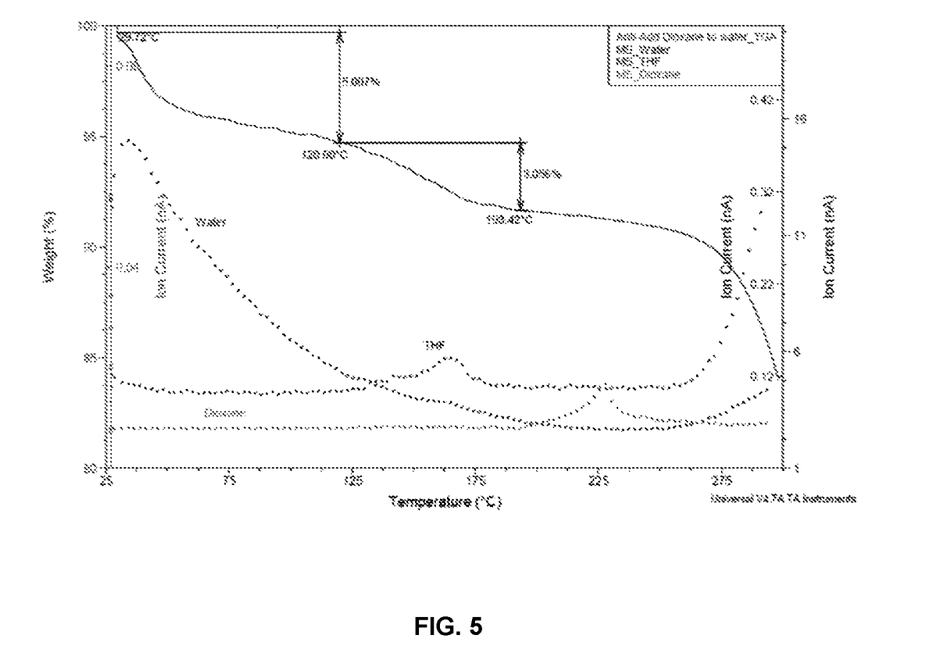
FIG. 5 illustrates a TGA-MS thermogram of compound 2 (Form 2A).
Figure 6:
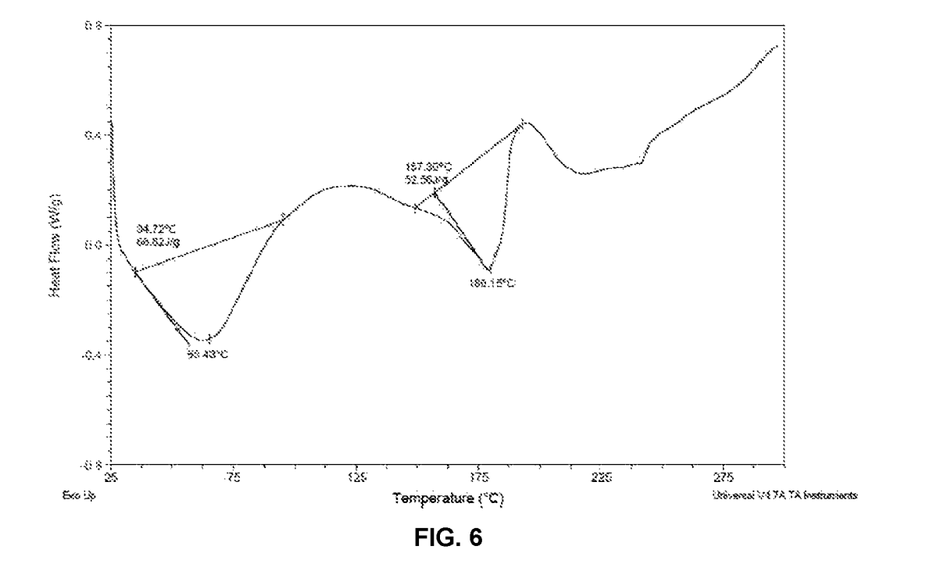
FIG. 6 illustrates a DSC thermogram of compound 2 (Form 2B).

In another embodiment, the present invention provides a pharmaceutical formulation comprising a crystalline form of mesylate salt designated as Form 2B, characterized by having one or more of the following characteristics:

(a) an X-ray powder diffraction pattern containing three or more of the following 2θ values measured using CuKα radiation: 9.7°±0.2°, 12.8°±0.2°, 15.7°±0.2°, 18.2°±0.2°, 20.3°±0.2°, 25.1°±0.2°, 25.6°±0.2°, and 26.8°±0.2°;

(b) an X-ray powder diffraction pattern substantially as depicted in FIG. 4A and FIG. 4B;

(c) a differential scanning calorimetric (DSC) thermogram substantially as depicted in FIG. 6; and/or (d) having a thermal gravimetric analysis thermogram substantially as depicted in FIG. 5.

The formulation of the present invention includes one or more pharmaceutically acceptable excipients. Non-limiting examples of excipients include filler, binder, disintegrant, lubricant, surfactant, pH modifier or any combination from these. In some embodiments, the excipients comprise one or more members selected from filler, binder, disintegrant, and lubricant. The amount of the excipient or excipients in the formulation ranges from about 10% to about 98%, all subranges included, by weight. Examples of the amount of the excipient or excipients include about 1%, about 5%, about 10%, about 15%, about 20%, about 30%, about 40%, about 50%, about 60%, about 70%, about 80%, about 90%, and about 95% by weight.

Suitable fillers include, but are not limited to, monohydrate lactose, anhydrous lactose, sucrose, dextrose, mannitol, sorbitol, starch, pregelatinized starch, cellulose (particularly microcrystalline cellulose), dihydrate or anhydrous dicalcium phosphate, calcium phosphate, calcium carbonate, and calcium sulfate. Each filler accounts for from about 15% to about 70%, from about 15% to about 60%, from about 15% to about 50%, from about 20% to about 60%, or from about 20% to about 50% of the formulation by weight. In some embodiments, the fillers comprise microcrystalline cellulose as a first filler and a second filler selected from the group consisting of monohydrate lactose, anhydrous lactose, sucrose, dextrose, mannitol, sorbitol, starch, pregelatinized starch, dihydrate or anhydrous dicalcium phosphate, calcium phosphate, calcium carbonate, and calcium sulfate.

Suitable binders include, but are not limited to, acacia, cellulose derivatives (e.g. methylcellulose, carboxymethylcellulose, hydroxypropylmethyl cellulose, hydroxypropylcellulose, hydroxyethylcellulose), gelatin, glucose, dextrose, xylitol, polymethacrylates, polyvinylpyrrolidone, sorbitol, starch, tragacanth, xanthane resin, alginates, magnesium-aluminum silicate, polyethylene glycol (PEG), and bentonite. Each binder accounts for from about 1% to about 50%, from about 5% to about 50%, from about 10% to about 50%, from about 5% to about 30%, or from about 5% to about 20% of the formulation by weight.

Suitable disintegrants include, but are not limited to, starch, pregelatinized starch, hydroxypropyl starch, sodium starch glycolate, sodium carboxymethylcellulose, croscarmellose sodium, alginates, aluminum silicates, crospovidone, and low-substituted hydroxypropyl cellulose. Each disintegrant accounts for from about 1% to about 10%, from about 1% to about 7%, from about 1% to about 5%, or from about 2% to about 4% of the formulation by weight. In some embodiments, the disintegrant consists of one, two, three, or four members selected from starch, pregelatinized starch, hydroxypropyl starch, sodium starch glycolate, sodium carboxymethylcellulose, croscarmellose sodium, alginates, aluminum silicates, crospovidone, and low-substituted hydroxypropyl cellulose.

Suitable lubricants include, but are not limited to, magnesium stearate, calcium stearate, talc ("talcum powder"), polyethylene glycol ("PEG"), polymers of ethylene oxide, sodium lauryl sulfate, magnesium lauryl sulfate, sodium oleate, sodium stearyl fumarate, and silicon dioxide. Each lubricant accounts for from about 1% to about 10%, from about 1% to about 7%, from about 1% to about 5%, or from about 2% to about 4% of the formulation by weight. In some embodiments, the lubricant consists of one, two, three, or four members selected from magnesium stearate, calcium stearate, talc ("talcum powder"), polyethylene glycol ("PEG"), polymers of ethylene oxide, magnesium lauryl sulfate, sodium oleate, sodium stearyl fumarate, and silicon dioxide. In some embodiments, the formulation is substantially free from sodium lauryl sulfate.

In one embodiment, sometimes preferred, the pharmaceutically acceptable excipients in the formulation comprise microcrystalline cellulose, dicalcium phosphate, sodium starch glycolate, silicon dioxide, and magnesium stearate.

In one embodiment, sometimes preferred, the pharmaceutically acceptable excipients in the formulation consist substantially of microcrystalline cellulose, dicalcium phosphate, sodium starch glycolate, silicon dioxide, and magnesium stearate. A specific example of the formulation of this type is the Formulation 1 substantially described in Example 3 and Table 1.

In one embodiment, sometimes preferred, the pharmaceutically acceptable excipients in the formulation comprise microcrystalline cellulose, lactose monohydrate, sodium lauryl sulfate, croscarmellose sodium, silicon dioxide, and magnesium stearate.

In one embodiment, sometimes preferred, the pharmaceutically acceptable excipients in the formulation consist substantially of microcrystalline cellulose, lactose monohydrate, sodium lauryl sulfate, croscarmellose sodium, silicon dioxide, and magnesium stearate. A specific example of the formulation of this type is the Formulation 2 substantially described in Example 4 and Table 2.

Examples of the dosage form of the present invention include a capsule, a tablet, sachet, or granule powder. A unit dosage form contains, for example, about 1 mg to about 1000 mg of compound 1 or a pharmaceutically acceptable salt thereof. Non-limiting examples of the amount of compound 1 or a pharmaceutically acceptable salt thereof in the unit dosage form include about 1 mg, about 5 mg, about 7.5 mg, about 10 mg, about 25 mg, about 35 mg, about 40, or about 50 mg. A dosage form may contain one or more unit dosage forms.

As used herein, the terms "methanesulfonic acid salt", "methanesulfonate salt", "mesylate salt", or the like are used interchangeably. They refer to an acid addition salt having a general formula 1.MeSO$_3$H, i.e., compound 2. Preferably, the salt contains compound 1 and methanesulfonic acid in 1:1 mole ratio, or substantially in 1:1 mole ratio. However, as a person of skill in the art would understand, the ratio may or may not be exactly 1:1; therefore, an addition salt of this type having a ratio between 1 and MeSO$_3$H in the range of 1:0.8 to 1:1.2 should be considered a salt of 1.MeSO$_3$H, which is preferably controlled within 1:0.9 to 1:1.1, and more preferably within 1:0.95 to 1:05 ratio. As a person of skill in the art would also understand, co-presence of compound 1 and methanesulfonic acid in any ratio would likely form a mesylate salt, i.e. compound 2, though depending on the ratio, either compound 1 or the acid may partially exist as a free base or free acid, respectively.

The mesylate salt of compound 1, depending on crystalline forms and the solvents from which it is generated, may be in the form of a solvate, i.e., containing a varying amount of solvent molecules, such as water (hydrate), methanol, THF, or the like. All of these salt forms or solvate forms may be formulated substantially using the methods disclosed herein, and they are all encompassed by the present invention.

Therapeutic Use of the Formulations

In another aspect, the present invention provides a method of treating a disease or disorder associated with an EGFR activity, the method comprising administration of a pharmaceutical formulation comprising a methanesulfonic acid salt of compound 1 according to any embodiments disclosed herein to a subject in need thereof.

In some embodiments, the disease or disorder is associated with one or more mutants of EGFR.

In some embodiments, the mutant or mutants of EGFR are selected from L858R activating mutants L858R, delE746-A750, G719S; the Exon 19 deletion activating mutant; and the T790M resistance mutant.

In some embodiments, the disease or disorder is a cancer.

In some embodiments, the cancer is selected from brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors, or their complications.

In some embodiments, the cancer is brain cancer or lung cancer.

In some embodiments, the cancer is a metastatic brain cancer.

As disclosed in International Application No. PCT/US2017/032066, which is incorporated herein by reference in its entirety, the compound 1 can be used for treatment of brain cancers, including metastatic brain cancer. Thus, the formulations of present invention are particularly useful for treatment of patients with these conditions. Particular useful formulations for these therapeutic uses include the Formulation 1 and Formulation 2 disclosed herein.

In some embodiments, any embodiment of the method of treating diseases or disorders is used in combination with administering to the patient a second therapeutic agent.

In some embodiments, the second therapeutic agent is a chemotherapeutic agent.

In some embodiments, the second therapeutic agent is a different EGFR modulator.

In another aspect, the present invention provides a method of inhibiting a mutant of EGFR in a subject, comprising contacting a biological sample of a patient with a formulation according to any embodiments disclosed herein.

In another aspect, the present invention provides use of a formulation according to any embodiments disclosed herein in the manufacture of a medicament for treatment of a disease or disorder associated with an EGFR activity.

In some embodiments of this aspect, the disease or disorder is a cancer selected from the group consisting of brain cancer, lung cancer, kidney cancer, bone cancer, liver cancer, bladder cancer, head and neck cancer, esophageal cancer, stomach cancer, colon cancer, rectum cancer, breast cancer, ovarian cancer, melanoma, skin cancer, adrenal cancer, cervical cancer, lymphoma, and thyroid tumors and their complications.

In some embodiments of this aspect, the disease or disorder is brain cancer or lung cancer.

In some embodiments, the formulation of present invention may be used for delaying the onset of the disease or disorder or preventing a disease, disorder or condition from occurring in a subject that may be predisposed to the disease, disorder, and/or condition but has not yet been diagnosed as having it.

Another aspect of the present invention provides methods processes of preparing formulations according to any embodiments disclosed herein as substantially described and shown.

Pharmaceutical formulations may be presented in unit dose forms containing a predetermined amount of active ingredient per unit dose. Typically, the pharmaceutical formulations of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing substantial harmful or deleterious side effects.

When the formulations of this disclosure comprise a combination of a crystalline form of compound 1 or a pharmaceutically acceptable salt thereof and one or more, preferably one or two, additional therapeutic or prophylactic agent(s), both the compound 1 and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example, by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Tablets are formulated, for example, by preparing a powder mixture, granulating or slugging, adding a lubricant and disintegrant, and pressing into tablets. A powder mixture is prepared, for example, by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax, or the like.

The following non-limiting Examples further illustrate certain aspects of the present invention.

EXAMPLES

Example 1

Preparation of Compound 1

N-(2-(2-(Dimethylamino)ethoxy)-4-methoxy-5-((4-(1-methyl-1H-indol-3-yl)pyrimidin-2-yl)amino)phenyl)acrylamide (1)

Step 1. A solution of 4-(2-(dimethylamino)ethoxy)-6-methoxy-N-1-(4-(1-methyl-1H-indol-3-yl)pyrimidin-2-yl)benzene-1,3 diamine (A, prepared as in International Application No. PCT/US15/65286; 1 equiv, 16.8 g, 26.2 mmol) in THF (550 mL) and water (120 mL) was cooled to 0-5° C. Acryloyl chloride (1.0 equiv., 3.3 mL) was added dropwise over 30 minutes. After 2 hours, additional acryloyl chloride (0.4 mL) was added over 10 minutes and the mixture was stirred for 1 h. NaOH (2 equiv., 2.8 g, 68.0 mmol) was added, and the mixture was stirred for 30 minutes, and then partially concentrated to remove THF. The aqueous phase was extracted with dichloromethane (900 mL), and the organic phase was dried $Na_2SO_4$ and concentrated. The crude product was purified via column chromatography (silica gel; dichloromethane/MeOH, 80:1 to 20:1 gradient) to afford compound 1 (14.0 g), which can be further purified according to Step 2, if needed.

Step 2. To a solution of compound 1, prepared as in Step 1, (1 eq, 22.5 g, 46.3 mmol), in 850 mL of THF was added NaOH (9 g dissolved in 203 mL of $H_2O$) over 5 min. The mixture was heated to 60° C. with stirring for 50 min, then cooled to 10-20° C. and 1N HCl (180 mL) was added over 20 min. The layers were separated and the aqueous phase was extracted with dichloromethane (2×400 mL). The organic phases were combined, dried ($Na_2SO_4$) and concentrated. The crude product was purified via column chromatography (silica gel; 20:1 dichloromethane/MeOH) to afford a solid, which was dissolved in dichloromethane/heptane (2:3) then concentrated to afford 19.5 g of compound 1 as a crystalline solid. $^1$H NMR (400 MHz, $CD_3OD$) δ ppm 2.42 (s, 6H), 2.80 (br t, J=5.0 Hz, 2H), 3.98 (s, 3H), 3.92 (s, 3H), 4.21 (br t, J=5.0 Hz, 2H), 5.79 (dd, J=10.2, 1.4 Hz, 1H), 6.39 (dd, J=16.9, 1.4 Hz, 1H), 6.64 (dd, J=16.9, 10.2 Hz, 1H), 6.83 (s, 1H), 7.15-7.30 (m, 3H), 7.46 (d, J=7.6 Hz, 1H), 8.16-8.30 (m, 2H), 8.52 (s, 1H), 9.29 (s, 1H).

Example 2

Preparation of Methanesulfonic Acid Salt (Compound 2, Crystalline Forms 2A and 2B)

N-(2-(2-(Dimethylamino)ethoxy)-4-methoxy-5-((4-(1-methyl-1H-indol-3-yl)pyrimidin-2-yl)amino)phenyl)acrylamide methanesulfonate (1:1) (2)

To a solution of 100 mg of compound 1 (free base) in 4 mL of THF was added a solution of 21.7 mg of methanesulfonic acid in 0.164 mL of water, and the solution was stirred at room temperature overnight. The precipitate was isolated by centrifugation at 8000 rpm for 5 mins. After drying under vacuum at 30° C. overnight, 60 mg of methanesulfonate salt, crystalline Form 2A, was obtained. $^1$H NMR (400 MHz, $CD_3OD$) δ ppm 2.73 (s, 3H), 3.06 (s, 6H), 3.65-3.72 (m, 2H), 3.94 (s, 3H), 4.00 (s, 3H), 4.54-4.60 (m, 2H), 5.86 (br d, J=10.0 Hz, 1H), 6.40-6.48 (m, 1H), 6.56-6.66 (m, 1H), 6.98 (s, 1H), 7.20-7.34 (m, 3H), 7.50 (d, J=8.0 Hz, 1H), 8.11 (br d, J=6.0 Hz, 1H), 8.35 (br d, J=7.8 Hz, 1H), 8.42 (s, 1H), 8.50 (br s, 1H). Anal. Calcd. for $C_{28}H_{34}N_6O_6S$: C, 57.72; H, 5.88; N, 14.42; 0, 16.47; S, 5.50. Found: C, 57.76; H, 5.85; N, 14.45; 0, 16.34; S, 5.60; $C_{27}H_{30}N_6O_3 \cdot 1.0$ $CH_3SO_3H$.

Form 2A is a beige crystalline powder; and its XRPD pattern is shown in FIG. 1. It shows birefringence and has a melting point with onset temperature at 233.3° C., ~0.40% weight loss before the melting point in the differential scanning calorimetry (DSC) analysis (FIG. 2) and 0.035% weight loss from 170° C. to 210° C. in the thermogravimetric analysis (TGA) (FIG. 3).

A polymorph screening study was performed on Form 2A by the slurry, solvent-thermal heating/cooling, anti-solvent precipitation, solid heating-cooling and grinding methods. One new crystal form, Form 2B, was obtained by precipitation from an aqueous solution using dioxane as antisolvent at room temperature. Form 2B may be a hydrate form of Form 2A and shows lower crystallinity, lower melting point and higher weight loss as compared with the Form 2A. XRPD, TGA-MS, and DSC analyses of Form 2B are shown in FIGS. 4, 5, and 6, respectively. Because of its apparent superior stability, while not intended to be limiting, crystalline Form 2A has been used for preparing formulations of the methanesulfonate salt (compound 2) in this application.

Example 3

Preparation of Formulation 1 of Methanesulfonate Salt (2)

Microcrystalline cellulose (392.43 mg), dicalcium phosphate (735.35 mg), sodium starch glycolate (45.09 mg), silicon dioxide (15.03 mg), and magnesium stearate (15.03 mg) were combined and blended with a vortex mixer in the amounts and proportions indicated in Table 1. The resulting mixture was filtered through a #35 mesh sieve to give Mixture A. A 20.05 mg portion of Mixture A was combined with 5.0 mg of 1·Ms ($C_{27}H_{30}N_6O_3 \cdot 1.06\ CH_3SO_3H$, purity=100%) of crystalline Form 2A in a 40 mL glass vial and blended thoroughly with a vortex mixer to afford Formulation 1, which has a theoretical composition as calculated in Table 1.

All samples were stored in a stability chamber at temperatures of −20° C., 50° C., and at 40° C./75% relative humidity for 2-week and 4-week periods and analyzed for stability. Closed-dish samples were capped and sealed with Parafilm. Open-dish samples were covered by aluminum foil that was pierced with a pinhole.

TABLE 1

Components of Formulation 1 of 1·Ms.

| # | Component | Percentage (%) | Amount (mg) |
|---|---|---|---|
|   | 1·Ms | 19.96 | 5.00 |
| 1 | Microcrystalline cellulose (filler) | 26.11 | 6.54 |
| 2 | Dicalcium phosphate (filler) | 48.93 | 12.26 |
| 3 | Sodium starch glycolate (disintegrate) | 3.00 | 0.75 |
| 4 | Silicon dioxide (lubricant) | 1.00 | 0.25 |
| 5 | Magnesium stearate (lubricant) | 1.00 | 0.25 |

Example 4

Preparation of Formulation 2 of Methanesulfonate Salt (2)

Formulation 2 of compound 2 was prepared and analyzed by substantially similar procedures as described above. Microcrystalline cellulose (545.23 mg), lactose monohydrate (495.71 mg), sodium lauryl sulfate (7.51 mg), croscarmellose sodium (42.58 mg), silicon dioxide (14.19 mg), and magnesium stearate (14.19 mg) were combined and blended with a vortex mixer in the amounts and proportions indicated in Table 1. Crystalline Form 2A was used in the preparation of all samples in this example. The resulting mixture was filtered through a #35 mesh sieve to give Mixture B. A 18.65 mg portion of Mixture B was combined with 5.0 mg of 1·Ms ($C_{27}H_{30}N_6O_3 \cdot 1.06\ CH_3SO_3H$, purity=100%) of crystalline Form 2A in a 40 mL glass vial and blended thoroughly with a vortex mixer to afford Formulation 1, which has a theoretical composition as calculated in Table 2. All samples were stored in a stability chamber at temperatures of −20° C., 50° C., and at 40° C./75% relative humidity for 2-week and 4-week periods and analyzed for stability.

Table 2

Components of Formulation 2 of 1·Ms.

| # | Component | Percentage (%) | Amount (mg) |
|---|---|---|---|
|   | 1·Ms | 21.14 | 5.00 |
| 1 | Microcrystalline cellulose | 38.41 | 9.08 |
| 2 | Lactose monohydrate (filler) | 34.92 | 8.26 |
| 3 | Sodium lauryl sulfate (lubricant) | 0.53 | 0.13 |
| 4 | Croscarmellose sodium (disintegrant) | 3.00 | 0.71 |
| 5 | Silicon dioxide | 1.00 | 0.24 |
| 6 | Magnesium stearate | 1.00 | 0.24 |

Example 5

Stability Testing of Formulation 1 of Methanesulfonate Salt

Figure 7:
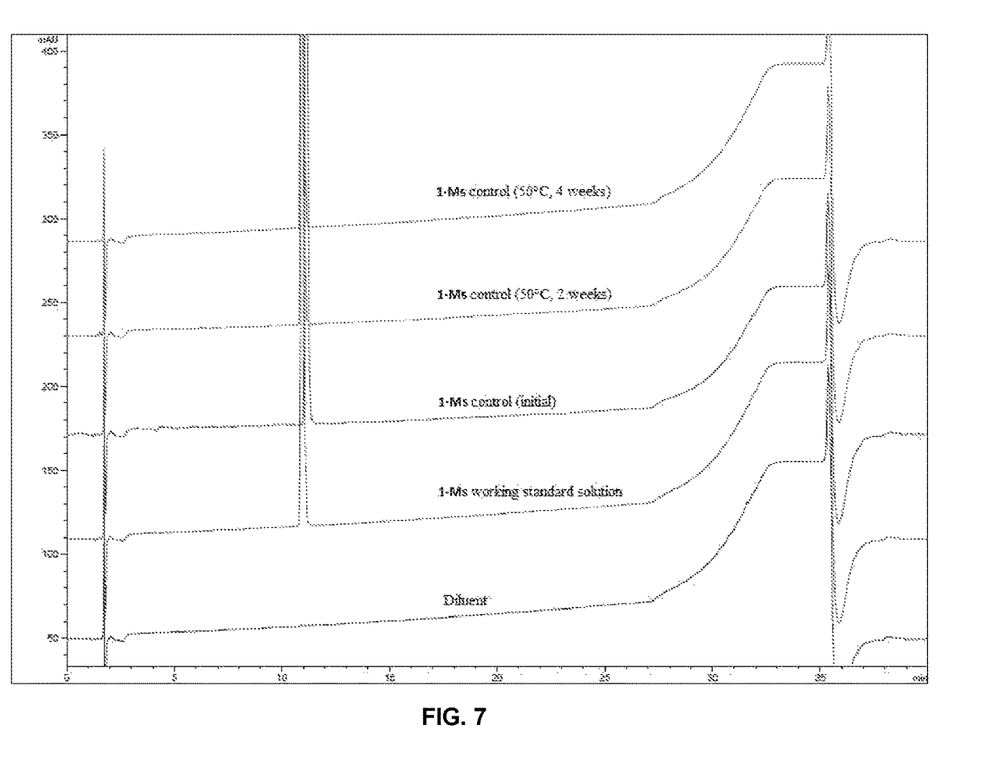
FIG. 7 illustrates the overlay of HPLC chromatograms of compound 2 as control in the stability testing of Formulation 1 at 50° C.
Figure 8:
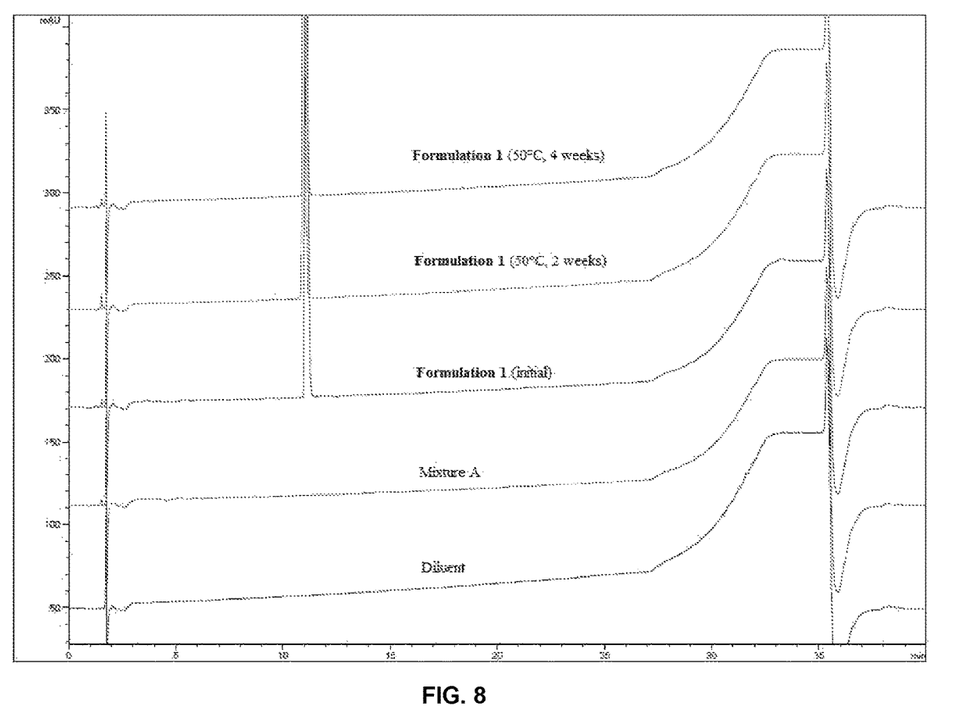
FIG. 8 illustrates the overlay of HPLC chromatograms from stability testing of Formulation 1 at 50° C.
Figure 9:
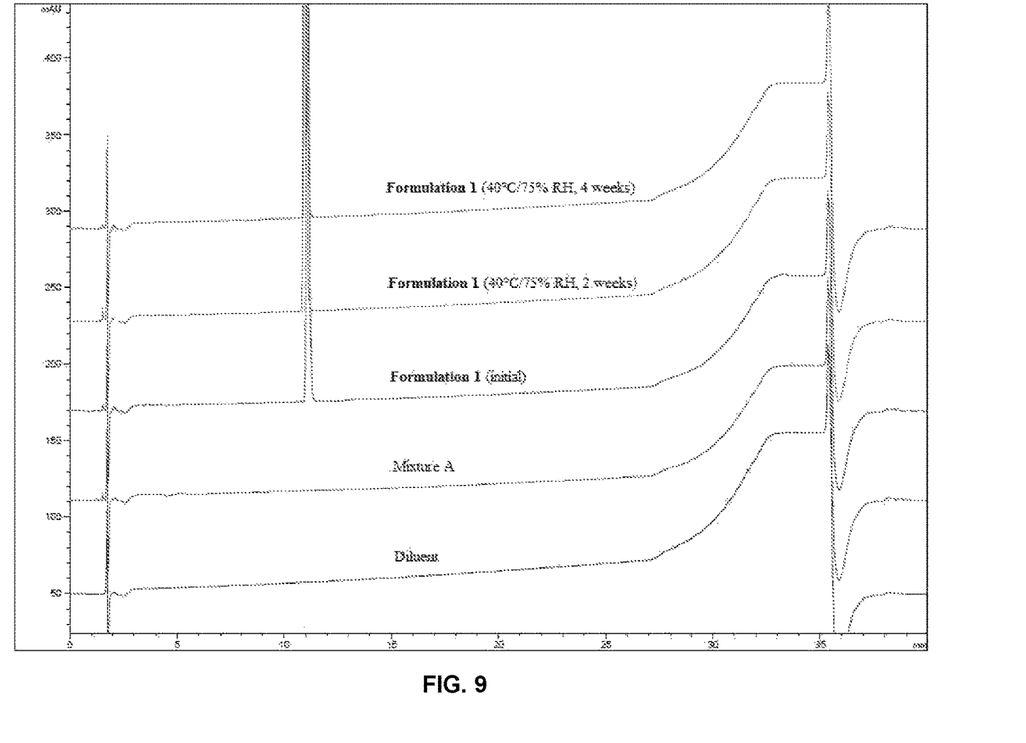
FIG. 9 illustrates the overlay of HPLC chromatograms from stability testing of Formulation 1 at 40° C. @ 75% relative humidity.

After reaching room temperature, each sample was added to a 40 mL sample vial containing 10 mL of diluent (0.05% TFA in $H_2O$:MeCN=1:1 v/v) and sonicated for 10 minutes with occasional shaking. All samples were centrifuged at 14,000 rpm for 10 minutes and the supernatant was analyzed by HPLC. The working standard solution (5 mg of 1·Ms in 10 mL of diluent) was used as a reference. Results for Formulation 1 are shown in Table 3, in which purity is measured as percent (%) versus total related substances (TRS). As shown in Table 1 and FIGS. 7 to 9, Formulation 1 was stable over an extended period. No degradation of compound 1 in the formulation was observed in a four week period at 50° C. or at 40° C./75% relative humidity.

TABLE 3

Stability of 1•Ms and Formulation 1

| | Initial | | 50° C. | | | | 40° C. @ 75% relative humidity | | | |
|---|---|---|---|---|---|---|---|---|---|---|
| | | | 2 weeks | | 4 weeks | | 2 weeks | | 4 weeks | |
| Sample | Assay (%) | TRS* (%) | Assay (%) | TRS* (%) | Assay (%) | TRS* (%) | Assay (%) | TRS* (%) | Assay (%) | TRS* (%) |
| 1 · Ms | 100.2 | 0.00 | 101.4 | 0.00 | 99.9 | 0.00 | 101.1 | 0.00 | 99.3 | 0.00 |
| Formulation 1 | 100.0 | 0.00 | 101.4 | 0.00 | 99.9 | 0.00 | 100.7 | 0.00 | 100.2 | 0.00 |

*TRS = total related substances.

It will be understood by those of skill in the art that numerous and various modifications can be made without departing from the spirit of the present invention. Therefore, it should be understood that the various examples and embodiments of the present invention described herein are illustrative only and not intended to limit the scope of the present invention.

What is claimed is:

1. A pharmaceutical formulation, comprising a crystalline methanesulfonic acid salt of the compound of Formula 1:

wherein the crystalline methanesulfonic acid salt contains the compound of formula 1 and methanesulfonic acid in substantially 1:1 mole ratio; and about 20% to about 50% microcrystalline cellulose.

2. The pharmaceutical formulation of claim 1, wherein the methanesulfonic acid salt is crystalline Form 2A having an X-ray powder diffraction pattern comprising the following 2θ values measured using CuKα radiation: 12.6°±0.2°, 15.5°±0.2°, 17.9°±0.2°, 22.1°±0.2°, and 25.2°±0.2°.

3. The pharmaceutical formulation of claim 2, wherein the crystalline Form 2A is further characterized by:
    (a) the X-ray powder diffraction pattern further comprising two or more of the following 2θ values measured using CuKα radiation: 11.1°±0.2°, 13.8°±0.2°, 14.7°±0.2°, 16.7°±0.2°, 19.3°±0.2°, 20.9°±0.2°, 23.2°±0.2°, and 25.8°±0.2°; and/or
    (b) the crystalline form having a melting point with an onset temperature at about 233.3° C. and/or a peak temperature at about 238.1° C. as measured by differential scanning calorimetry.

4. The pharmaceutical formulation of claim 1, wherein the methanesulfonic acid salt is crystalline Form 2B having an X-ray powder diffraction pattern comprising the following 2θ values measured using CuKα radiation: 12.8°±0.2°, 15.7°±0.2°, 18.2°±0.2°, 20.3°±0.2°.

5. The pharmaceutical formulation of claim 4, wherein the crystalline Form 2B is further characterized by
    the X-ray powder diffraction pattern comprising one or more of the following 2θ values measured using CuKα radiation: 9.7°±0.2°, 25.1°±0.2°, 25.6°±0.2°, and 26.8°±0.2°.

6. The pharmaceutical formulation of claim 1, wherein the formulation comprises about 10% to about 30% by weight of the methanesulfonic acid salt of the compound of Formula 1.

7. The pharmaceutical formulation of claim 2, wherein the formulation comprises about 10% to about 30% by weight of the methanesulfonic acid salt of the compound of Formula 1.

8. The pharmaceutical formulation of claim 1, further comprising one or more fillers independently selected from the group consisting of monohydrate lactose, anhydrous lactose, sucrose, dextrose, mannitol, sorbitol, starch, pregelatinized starch, dihydrate or anhydrous dicalcium phosphate, calcium phosphate, calcium carbonate, and calcium sulfate, wherein each of said fillers accounts for about 15% to about 50% of the formulation by weight.

9. The pharmaceutical formulation of claim 1, further comprising one or more disintegrants selected from the group consisting of starch, pregelatinized starch, hydroxypropyl starch, sodium starch glycolate, sodium carboxymethylcellulose, croscarmellose sodium, alginates, aluminum silicates, crospovidone, and hydroxypropyl cellulose, wherein each of said disintegrants accounts for about 1% to about 10% of the formulation by weight.

10. The pharmaceutical formulation of claim 1, further comprising one or more lubricants selected from the group consisting of magnesium stearate, calcium stearate, talc ("talcum powder"), polyethylene glycol ("PEG"), polymers of ethylene oxide, sodium lauryl sulfate, magnesium lauryl sulfate, sodium oleate, sodium stearyl fumarate, and silicon dioxide, wherein each of said lubricants accounts for about 1% to about 10% of the formulation by weight.

11. The pharmaceutical formulation of claim 1, further comprising one or more binders selected from the group consisting of acacia, methylcellulose, carboxymethylcellulose, hydroxypropylmethylcellulose, hydroxypropylcellulose, hydroxyethylcellulose, gelatin, glucose, dextrose, xylitol, polymethacrylates, polyvinylpyrrolidone, sorbitol, starch, tragacanth, xanthane resin, alginates, magnesium-aluminum silicate, polyethylene glycol (PEG), and bentonite, wherein each of said binders accounts for about 5% to about 30% of the formulation by weight.

12. The pharmaceutical formulation of claim 1, further comprising dicalcium phosphate, sodium starch glycolate, silicon dioxide, and magnesium stearate.

13. The pharmaceutical formulation of claim 12, wherein the methanesulfonic acid salt of the compound of Formula 1 is in crystalline Form 2A having (a) an X-ray powder diffraction pattern comprising the following 2θ values measured using CuKα radiation: 11.1°±0.2°, 12.6°±0.2°, 13.8°±0.2°, 14.7°±0.2°, 15.5°±0.2°, 16.7°±0.2°, 17.9°±0.2°, 19.3°±0.2°, 20.9°±0.2°, 22.1°±0.2°, 23.2°±0.2°, 25.2°±0.2°, and 25.8°±0.2°; and/or (b) a melting point with an onset temperature at about 233.3° C. and/or a peak temperature at about 238.1° C. as measured by differential scanning calorimetry.

14. The pharmaceutical formulation of claim 13, consisting essentially of about 20 wt % of the methanesulfonic acid salt of the compound of Formula 1 in crystalline Form 2A, about 26 wt % of microcrystalline cellulose, about 49 wt % of dicalcium phosphate, about 3 wt % of sodium starch glycolate, about 1 wt % of silicon dioxide, and about 1 wt % of magnesium stearate.

15. The pharmaceutical formulation of claim 1, comprising
    about 10 wt % to about 30 wt % of the crystalline methanesulfonic acid salt;
    about 20% to about 50% microcrystalline cellulose;
    about 20% to about 50% of calcium diphosphate, lactose monohydrate, or anyhydrous lactose;
    about 1% to about 5% disintegrant; and
    about 1% to about 5% lubricant.

* * * * *